US012697073B2

(12) United States Patent     (10) Patent No.: US 12,697,073 B2

Howard     (45) Date of Patent: Aug. 4, 2026

(54) METHOD FOR DETECTING VIROLOGICAL DISORDERS

(71) Applicant: Genesis Intelligence, LLC, Jacksonville, FL (US)

(72) Inventor: Newton Howard, Potomac, MD (US)

(73) Assignee: Genesis Intelligence, LLC, Jacksonville, FL (US)

( * ) Notice: Subject to any disclaimer, the term of this patent is extended or adjusted under 35 U.S.C. 154(b) by 597 days.

(21) Appl. No.: 18/055,055

(22) Filed: Nov. 14, 2022

(65) Prior Publication Data

US 2023/0172560 A1     Jun. 8, 2023

Related U.S. Application Data

(60) Provisional application No. 63/278,716, filed on Nov. 12, 2021.

(51) Int. Cl.
*G06T 7/00*     (2017.01)
*A61B 5/00*     (2006.01)
    (Continued)

(52) U.S. Cl.
CPC .......... *A61B 5/7267* (2013.01); *A61B 5/7282* (2013.01); *A61B 6/5217* (2013.01);
    (Continued)

(58) Field of Classification Search
CPC ... A61B 5/7267; A61B 5/7282; A61B 6/5217; A61B 5/055; G06T 7/0012;
    (Continued)

(56) References Cited

U.S. PATENT DOCUMENTS

2022/0022818 A1*   1/2022   Ghesu ................... A61B 5/7275
2022/0039768 A1*   2/2022   Wang ................... G06N 3/0475
    (Continued)

OTHER PUBLICATIONS

Sedik, Ahmed, et al. "Deploying machine and deep learning models for efficient data-augmented detection of COVID-19 infections." Viruses 12.7 (2020): 769. (Year: 2020).*

*Primary Examiner* — Van D Huynh
(74) *Attorney, Agent, or Firm* — Neo IP

(57) ABSTRACT

Embodiments may relate to techniques for image augmentation used for the detection and screening of respiratory diseases, such as COVID-19 pneumonia. For example, For example, in an embodiment a system for detecting medical conditions may comprise an image acquisition component adapted to acquire a plurality of images of persons, at least some of whom have a medical condition, an image augmentation component adapted to generate a plurality of additional images from the acquired plurality of images using a plurality of image augmentation methods, and a training component adapted to train a machine learning model using the acquired plurality of images and the generated plurality of additional images to form a trained machine learning mode, wherein when the medical condition is COVID-19, not generating the plurality of additional images so as to improve accuracy of the machine learning model in recognizing presence or absence of COVID-19 in images.

12 Claims, 8 Drawing Sheets

(51) Int. Cl.
    *A61B 6/00*       (2006.01)
    *A61B 5/055*     (2006.01)

(52) U.S. Cl.
    CPC ............ G06T 7/0012 (2013.01); *A61B 5/055* (2013.01); *G06T 2207/10081* (2013.01); *G06T 2207/10088* (2013.01); *G06T 2207/10116* (2013.01); *G06T 2207/20081* (2013.01)

(58) Field of Classification Search
    CPC . G06T 2207/10081; G06T 2207/10088; G06T 2207/10116; G06T 2207/20081; G06T 2207/20084; G06T 2207/30061; G06N 3/0464; G06N 3/082; G06N 3/096
    See application file for complete search history.

(56)             References Cited

U.S. PATENT DOCUMENTS

| | | | | |
|---|---|---|---|---|
| 2022/0222812 A1* | 7/2022 | Li | .......................... | G06T 7/0012 |
| 2022/0244269 A1* | 8/2022 | Ireton | .................. | A61K 39/215 |
| 2022/0328189 A1* | 10/2022 | Zhou | ..................... | G06V 10/82 |
| 2023/0076809 A1* | 3/2023 | Chaudhary | .......... | A61B 6/5217 |

* cited by examiner

Fig. 6

|  | | Method I (Aug) Correct | Method I (Aug) Incorrect |
|---|---|---|---|
| Method II (No Aug) | Correct | A 5388 | B 346 |
| Method II (No Aug) | Incorrect | C 81 | D 39 |

McNemar's statsitc = 163.2

$p$-value = $2.23 \times 10^{-37}$    ($p \ll 0.0001$)

METHOD FOR DETECTING VIROLOGICAL DISORDERS

CROSS-REFERENCE TO RELATED APPLICATIONS

This application claims the benefit of U.S. Provisional Application No. 63/278,716, filed Nov. 12, 2021, the contents of which are incorporated herein in their entirety.

BACKGROUND

The present invention may relate to techniques for image augmentation used for the detection and screening of respiratory diseases, such as COVID-19 pneumonia.

Chest X-ray imaging technology used for the early detection and screening of COVID-19 pneumonia is both accessible worldwide and affordable compared to other non-invasive technologies. Additionally, deep learning methods have recently shown remarkable results in detecting COVID-19 on chest X-rays, making it a promising screening technology for COVID-19. Deep learning relies on a large amount of data to avoid overfitting. While overfitting can result in perfect modeling on the original training dataset, on a new testing dataset it can fail to achieve high accuracy. In the image processing field, an image augmentation step (i.e., adding more training data) is often used to reduce overfitting on the training dataset, and improve prediction accuracy on the testing dataset. However, the impact of geometric augmentations on the performance of deep learning algorithms is not necessarily positive.

Accordingly, a need arises for imaging technology for detection of COVID-19 infection that has improved detection performance.

SUMMARY

The present invention may relate to techniques for image augmentation used for the detection and screening of respiratory diseases, such as COVID-19 pneumonia.

For example, in an embodiment a system for detecting medical conditions may comprise an image acquisition component adapted to acquire a plurality of images of persons, at least some of whom have a medical condition, an image augmentation component adapted to generate a plurality of additional images from the acquired plurality of images using a plurality of image augmentation methods, and a training component adapted to train a machine learning model using the acquired plurality of images and the generated plurality of additional images to form a trained machine learning mode, wherein when the medical condition is COVID-19, not generating the plurality of additional images so as to improve accuracy of the machine learning model in recognizing presence or absence of COVID-19 in images.

In embodiments, the plurality of image augmentation methods may comprise at least some of: translation in x-axis, translation in y-axis, random shear in x-axis, random shear in y-axis, random rotation, horizontal reflection, vertical reflection, scaling in x-axis, scaling in y-axis, and any combination thereof. The acquired plurality of images may comprise at least one of X-ray images, CT images, and MRI images.

For example, in an embodiment a method for detecting medical conditions, implemented in a computer system comprising a processor, memory accessible by the processor, and program instructions and data stored in the memory to implement the method that may comprise: acquiring a plurality of images of persons, at least some of whom have a medical condition, generating a plurality of additional images from the acquired plurality of images using a plurality of image augmentation methods, and training a machine learning model using the acquired plurality of images and the generated plurality of additional images to form a trained machine learning model, wherein when the medical condition is COVID-19, not generating the plurality of additional images so as to improve accuracy of the machine learning model in recognizing presence or absence of COVID-19 in images.

For example, in an embodiment a non-transitory computer program product for detecting medical conditions, the computer program product comprising a non-transitory computer readable storage having program instructions embodied therewith, the program instructions executable by a computer, to cause the computer to perform a method that may comprise: acquiring a plurality of images of persons, at least some of whom have a medical condition, generating a plurality of additional images from the acquired plurality of images using a plurality of image augmentation methods, and training a machine learning model using the acquired plurality of images and the generated plurality of additional images to form a trained machine learning model, wherein when the medical condition is COVID-19, not generating the plurality of additional images so as to improve accuracy of the machine learning model in recognizing presence or absence of COVID-19 in images.

BRIEF DESCRIPTION OF THE DRAWINGS

The details of the present invention, both as to its structure and operation, can best be understood by referring to the accompanying drawings, in which like reference numbers and designations refer to like elements.

FIG. 6 is an exemplary comparison of accuracy of prediction methods according to embodiments of the present techniques.

DETAILED DESCRIPTION

Figure 1:
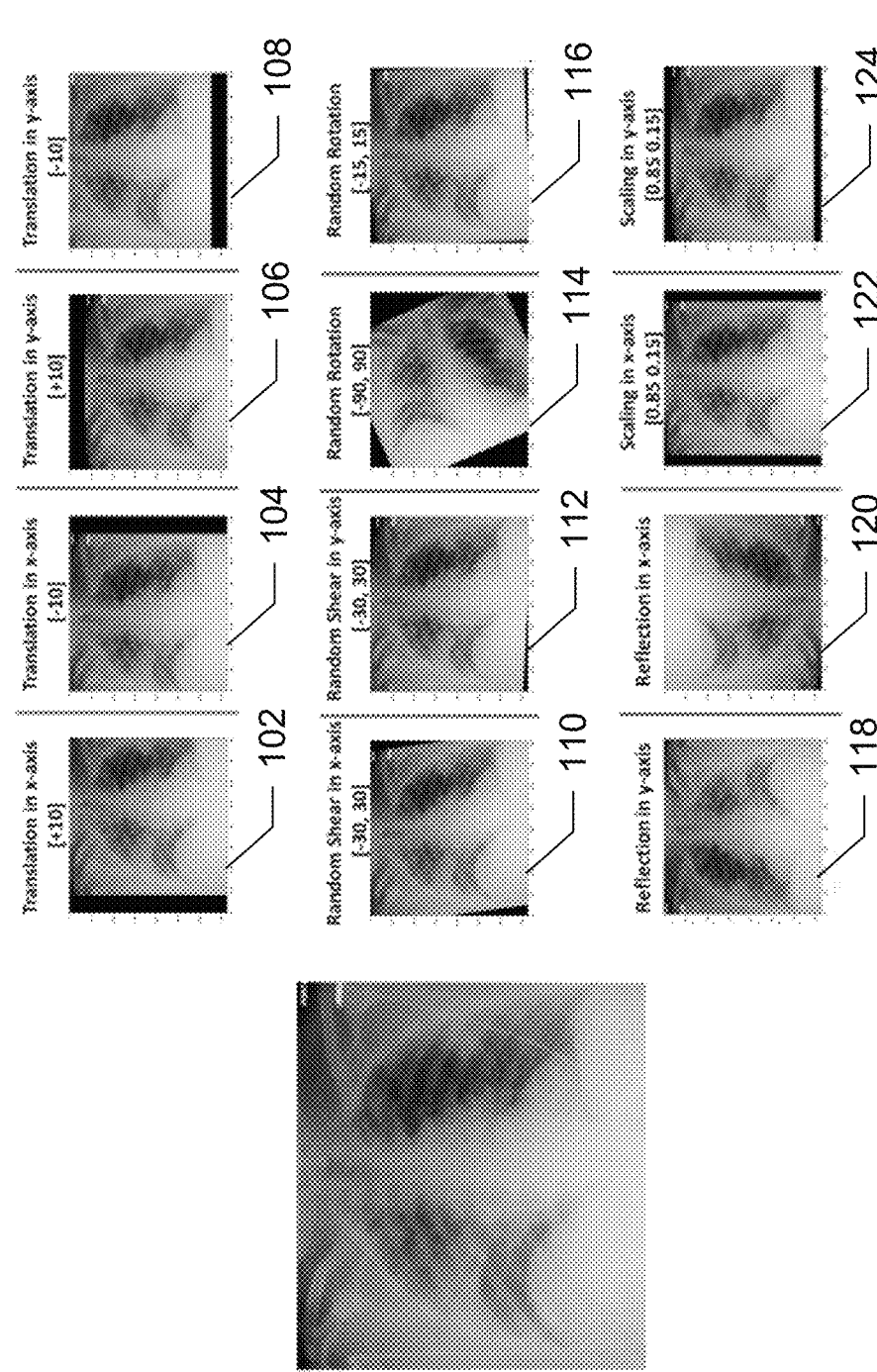
FIG. 1 shows geometric augmentations that may be applied individually, or in combination, to a COVID-19 X-ray image, according to embodiments of the present techniques.

The present invention relates to a techniques for image augmentation used for the detection and screening of respiratory diseases, such as COVID-19 pneumonia.

More people are being infected with COVID-19 every day; therefore there is a need for a quick and reliable technology to help with the screening and management of the virus. Recent research has shown that the combination of deep learning and chest X-rays could be faster and less expensive than the gold standard for COVID-19 diagnosis, which is a laboratory technique called reverse transcriptase polymerase chain reaction (PCR). It is therefore expected that this area of research will attract more researchers and that more papers will be published on this topic. Deep learning provides the ability to learn and nonlinearly associate high-dimensional features in X-ray images that feature COVID-19. One of the techniques used during the training and testing phases is data augmentation, which is used to make the deep learning model more robust to different types of noise, as well as increase the training dataset, which is typically needed in clinical applications.

It should be noted that data augmentation is commonly used in binary classification in cases where a large imbalance exists between the size of the two classes being used in a machine learning model. Algorithms such as SMOTE may be used to augment the minority class by intelligently synthesizing new data without overfitting. There are two ways to apply data augmentation: (1) class-balancing over-sampling (number of synthesized images more than in the training dataset), (2) replacement (number of synthesized images equals the number of images in the training dataset). The former is the most used data augmentation approach, which is being used to boost the number of images; however, the use of the latter approach is not clearly known. Embodiments may, for example, utilize the impact of data augmentation with replacement.

Recent techniques for COVID-19 detection from chest X-rays have used several data augmentation techniques to improve the testing accuracies of deep learning models, including random rotation, translation, and horizontal flipping. In some cases, two methods (translation and rotation) have been used at the same time. In contrast, other techniques have attempted to apply deep learning without a data augmentation step, which has created uncertainty over the use of data augmentation for detecting COVID-19 specifically, as well as for detecting abnormalities in X-Ray images in general. Embodiments may determine and utilize the impact of the augmentation step on detecting COVID-19 using X-ray images.

METHOD. To test the efficacy of the augmentation step, we examined a recently published deep learning method, DarkNet-19, with and without data augmentation. The analysis was carried out using MATLAB 2020a on a workstation (GPU NVIDIA Geforce RTX 2080Ti 11 GB, RAM 64 GB, and Intel Processor 19-9900K @3.6 GHz).

DATASETS. We created three datasets based on a publicly available dataset and two local datasets. The publicly available dataset is called "CoronaHack—Chest X-Ray-Dataset" (CHC-Xray; downloaded from https://www.kaggle.com/praveengovi/coronahack-chest-xraydataset). The first local dataset was collected from Vancouver General Hospital (VGH), British Columbia, Canada, and contains 58 COVID-19 X-ray images. The second local dataset was collected by the Department of Radiology at Louisiana State University (LSU), USA, and contains 374 coincident CXR and PCR tests evaluated for 366 individual patients. The clinical characteristics of the 366 patients at the time of RT-PCR testing include: 178/366 male (49%) and 188/366 female (51%) patients, with a mean age of 52.7 years (range 17-98 years). Average patient body mass index (BMI) was 32.0±9.7 kg/m2. All X-ray images were used from the LSU dataset, no image was excluded.

The datasets used in the training and validation stages of our study are defined as follows:

Dataset 1 was formed from CHC-Xray and consisted of 100 X-ray images (COVID=50, healthy=16, bacterial pneumonia=16, non-COVID-19 viral pneumonia=18).

Dataset 2 was formed from LSU and consisted of 374 X-ray images (COVID=198, non-COVID=176)

Dataset 3 was formed from CHC+LSU and consisted of 474 X-ray images (COVID=248, non-COVID=226)

Dataset 4 was formed as a testing dataset based on a previous publication, which combined CHC-Xray and VGH datasets, with a total of 5,854 X-ray images (COVID=58, healthy=1,560, bacterial pneumonia=2, 761, non-COVID-19 viral pneumonia=1,475). Note that Dataset 1 was used for training and validation during the development of the COVID-19 algorithm and therefore it is used to retrain and revalidate the same algorithm without augmentation.

DATA AUGMENTATION. The data augmentation steps examined in this study have been used in the literature for detecting COVID-19. Data augmentation procedures are intrinsically arbitrary and their justification is based upon empirical considerations (i.e., model performance) rather than fixed clinical considerations. Here, we will examine different data augmentation methods used recently in the literature. Our objective is to understand the impact of data augmentation and better understand whether one form of data augmentation is more useful than another. Four data augmentation methods proposed by Yoo et al., Nishio et al., Ahuja et al., and Zhang et al., implemented as follows:

Data Augmentation 1: This augmentation step is proposed by Nishio et al., which includes rotation within the range [−15, 15], translation in x- and y-axis within the range [−15, 15], horizontal flipping, scaling, and shear within the range 85-115%. The pseudo code for this augmentation method is as follows:

```
"RandRotation," [−15 15], . . .
"RandScale," [0.85 1.15], . . .
"RandYReflection," true, . . .
"RandXShear," [−floor(0.1*inputSize)
floor(0.1*inputSize)], . . .
"RandYShear," [−floor(0.1*inputSize)
floor(0.1*inputSize)], . . .
"RandXTranslation,"
[−floor(0.15*inputSize)
floor(0.15*inputSize)], . . .
"RandYTranslation,"
[−floor(0.15*inputSize)
floor(0.15*inputSize)]
```

Data Augmentation 2: This augmentation step is proposed by Ahuja et al., which includes shear operation within the range [−30, 30], random rotation within the range [−90, 90], and random translation from pixel range [−10, 10]. The pseudo code for this augmentation method is as follows:

```
"RandRotation," [−90 90], . . .
"RandXShear," [−30 30], . . .
"RandYShear," [−30 30], . . .
"RandXTranslation," [−10 10], . . .
"RandYTranslation," [−10 10]
```

Data Augmentation 3: This augmentation step is proposed by Zhang et al., which includes random rotation (30-degree range) and horizontal flipping. The pseudo code for this augmentation method is as follows:

"RandRotation," [−30 30], . . .

"RandYReflection," true'

Data Augmentation 4: This augmentation step is proposed by Yoo et al., which includes random rotation by 10 degree, translation, and horizontally flipping. The pseudo code for this augmentation method is as follows:

"RandRotation," [−10 10], . . .

"RandYReflection," true', . . .

"RandXTranslation," [−floor(0.2*inputSize)

floor(0.2*inputSize)], . . .

"RandYTranslation,"

[−floor(0.2*inputSize)

floor(0.2*inputSize)]

DEEP LEARNING ALGORITHMS. We investigated 17 pretrained neural networks: AlexNet, SqueezeNet, Google-Net, ResNet-50, DarkNet-53, DarkNet-19, ShuffleNet, Nas-Net-Mobile, Xception, Place365-GoogLeNet, MobileNet-v2, DenseNet-201, ResNet-18, Inception-ResNet-v28, Inception-v3, ResNet-101, and VGG-19. Each one of these pretrained neural networks has millions of parameters, and were originally trained to detect 1000 classes. Data augmentation and dropout were applied to all 17 networks, as part of the transfer learning that helps to combat overfitting. This make these pretrained neural networks ideal for testing the efficacy of data augmentation. Dataset 1, Dataset 2, and Dataset 3 were used with cross validation K=10, as it is based on experimental work to reduce both bias and variance.

To use each pretrained network, the last fully-connected layer, also known as the last convolutional layer, is replaced with the number of filters equal to the number of classes. At this stage, we set the training parameters for the analysis using the same setting used a recently published work. We set the filter size to 1,1 and changed the number of filters to two based on the number of classes in the analysis (COVID-19 and Others). To ensure learning was faster in the new layer than in the transferred layers, we changed the learning rates by setting both "WeightLearnRateFactor" and "BiasLearnRateFactor" to 10. We set the solver to be "sgmd," "InitialLearnRate" to 0.0001, ValidationFrequency to 5, and "MiniBatchSize" to 11. A recent study showed that setting the "MaxEpochs" to 8 is sufficient for preventing overfitting, for reporting steady learning, and for generalizing a classifier.

EVALUATION MEASURES. To evaluate the performance of the 17 deep learning algorithm over the three datasets (Dataset 1, Dataset 2, and Dataset 3), accuracy and Matthews correlation coefficient (MCC) will be used. The accuracy is considered as the most popular adopted metrics in binary classification tasks; however, for imbalanced datasets, such as the case in our work, the MCC is recommended. Moreover, to confirm statical significance Wilcoxon rank sum is used.

To evaluate the performance of recently published model with and without augmentation, McNemar's test will be used. Note that the recently published model is referred to as Method I, while the same model without augmentation is referred to as Method II in this work. The null hypothesis two models performs better than the other. Thus, we might consider the alternative hypothesis to be that the performances of the two models are not equal. However, in order to quantify and ensure that there is a significance between Method I and Method II, McNemar's test is applied. Precisely we applied the corrected McNemar's test as recommended in, as follows:

$$= \frac{(|B - C| - 1)^2}{B + C} \tag{1}$$

where $\chi^2$ is the corrected McNemar's statistic, B is the number of X-ray images that were detected correctly by Method II and incorrectly detected by Method I, while C is the number of X-ray images that were detected correctly by Method I and incorrectly by Method II.

RESULTS AND DISCUSSION Geometric augmentations are usually applied in combination to generate new augmented X-ray images. FIG. 1 shows geometric augmentations that are applied individually, or in combination, to a COVID-19 X-ray image. This visualizes the impact of each geometric augmentation method and gives the reader an idea about their relevance. FIG. 1 illustrates the application of different geometric augmentation transformations to a COVID-19 X-ray image. As shown, FIG. 1 demonstrates 12 different exemplary augmentation methods. From left-right and top-down these are: translation in x-axis with +10 pixels 102, translation in x-axis with −10 pixels 104, translation in y-axis with +10 pixels 106, translation in y-axis with −10 pixels 108, random shear in x-axis within the range [−30,30] 110, random shear in y-axis within the range [−30,30] 112, random rotation within the range [−90,90] 114, random rotation within the range [−15,15] 116, horizontal reflection (or flipping) 118, vertical reflection (or flipping) 120, scaling in x-axis [0.85 1.15] 122, and scaling in y-axis [0.85 1.15] 124. Any of these augmentations, or any others, may be applied, as well as and any combination thereof.

Table 1 shows the accuracy results of the four augmentation methods described above and the accuracy without applying the augmentation over three datasets. For simplicity, each geometrical augmentation transformation is presented in a separate column, as suggested in. The results show that data augmentation is not a required step and actually harmed the deep learning model in this case, by exposing it to a large amount of distorted (or noise) images. All augmentation methods scored lower validation accuracy than without augmentation. In other words, the augmenter trained the network on rotated and translated X-ray images that do not exist in a real-world scenario. To date, and to our current clinical knowledge, radiographic opacities associated with COVID-19 do not have a particular shape, size, or location. This in effect means geometric augmentation provides no added benefit, and can serve to reduce validation accuracy as shown here.

TABLE 1

Comparison of augmentation steps using three datasets.

| | Augmentation | | | | |
|---|---|---|---|---|---|
| | None | DA 1 | DA 2 | DA 3 | DA 4 |
| Reflection | — | √ | — | √ | √ |
| Scaling | — | √ | — | — | — |
| Shearing | — | √ | √ | — | — |
| Translation | — | √ | √ | — | √ |
| Rotation | — | √ | √ | √ | √ |
| Matthews correlation coefficient average (standard deviation) | | | | | |
| Dataset 1 CHC | 0.93 (0.05) | 0.87 (0.1) | 0.8 (0.15) | 0.87 (0.09) | 0.91 (0.05) |
| Dataset 2 LSU | 0.24 (0.06) | 0.19 (0.06) | 0.2 (0.06) | 0.21 (0.04) | 0.21 (0.04) |
| Dataset 3 LSU + CHC | 0.37 (0.05) | 0.35 (0.04) | 0.33 (0.05) | 0.34 (0.07) | 0.34 (0.06) |
| Average (standard deviation) | 0.51 (0.37) | 0.47 (0.35) | 0.44 (0.32) | 0.48 (0.35) | 0.49 (0.37) |

The Matthews correlation coefficient (MCC) is used as an evaluation measure. An MCC coefficient of +1 represents a perfect prediction while −1 indicates total disagreement between prediction and observation. The average of 17 MCCs obtained from 17 deep learning algorithms with cross validation K=10 is reported.

Data Augmentation 4 outperformed the other three augmentation methods on three datasets, with an overall MCC=0.49, suggesting that rotation, translation, and flipping could be used. On the contrary, Data Augmentation 2 scored the lowest validation MCC on the three datasets, with an overall MCC=0.44, suggesting that a combination of rotation, translation, and shear are "not recommended" as an augmentation step during the process of developing a COVID-19 detector. We will focus on analyzing the behavior of Data Augmentation 2 and Data Augmentation 4; the former is worst, and the latter is the best relative to the four augmentation methods tested. Note that Data Augmentation 4, which scored the highest validation MCC compared to the other augmentation methods, did not outperform without augmentation.

Figure 2:
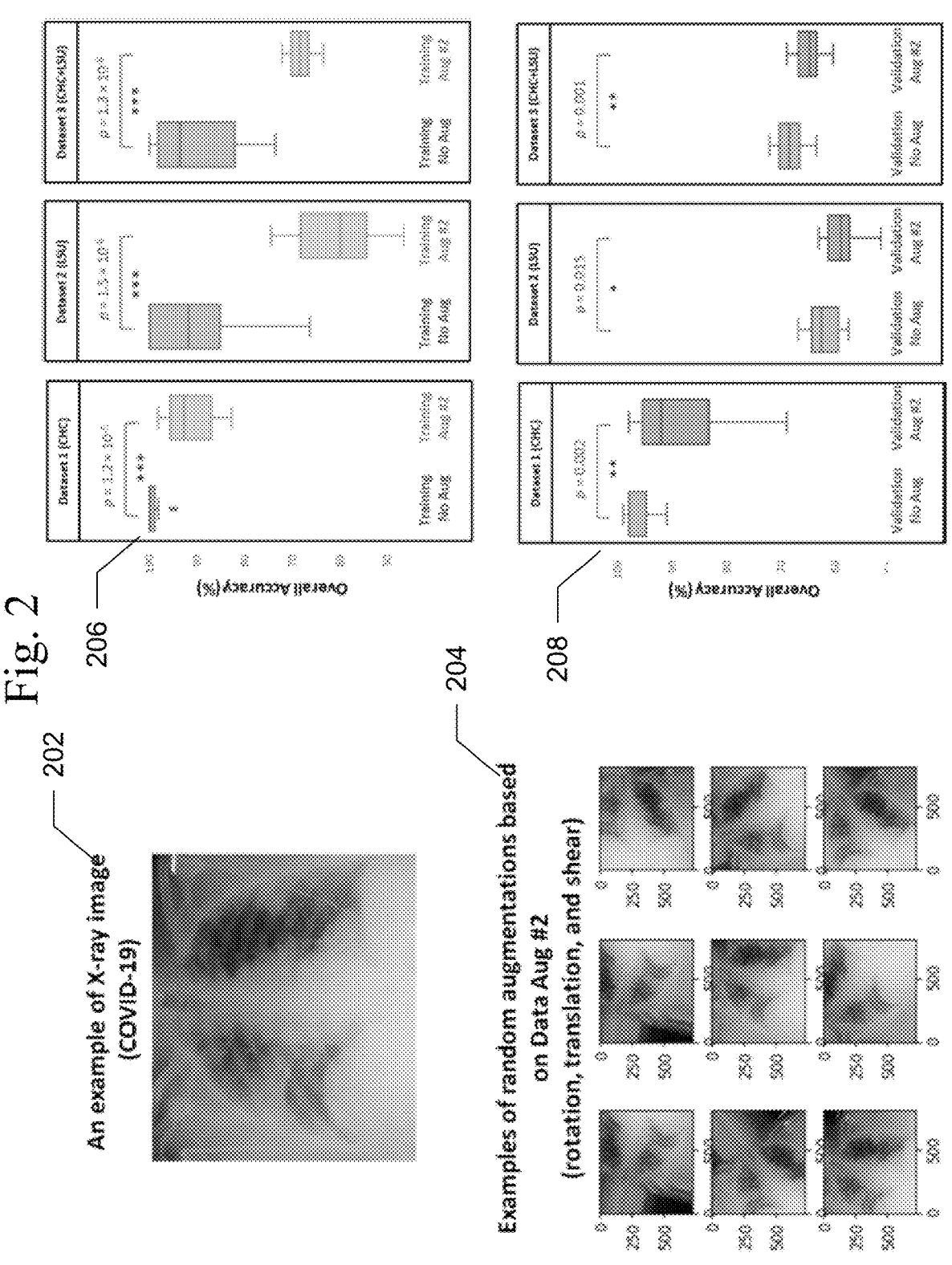
FIG. 2 shows the efficacy of an exemplary Data Augmentation on X-ray images with and without COVID-19, according to embodiments of the present techniques.

FIG. 2 shows the efficacy of Data Augmentation 2 on X-ray images with and without COVID-19. An example 202 of applying Data Augmentation 2, which includes shear operation within the range [−30, 30], random rotation within the range [−90, 90], and random translation from pixel range [−10, 10] to a COVID-19 X-ray image. At 204, the overall accuracy of 17 deep neural networks is compared to examine the efficacy of Data Augmentation 2 when applied to three datasets. Boxplots 206 show the overall statical different between training with and without augmentation over three datasets. Boxplots 208 show the overall statical different between validation with and without augmentation. Note that results shown at 206, 208 are obtained from cross validation with K=10.

FIG. 2 shows an example of X-ray image 202 for a subject diagnosed with COVID-19 using PCR. Examples of random outputs for applying Augmentation 2 to image 202 are shown at 204. The overall training accuracy with Augmentation 2 is significantly lower (p<<0.0001 in all datasets) than the training accuracy without any augmentation method over three datasets, as shown at 206. However, the same finding was observed over the validation accuracy, with significance (p=0.002, p=0.015, p=0.001, for Dataset 1, Dataset 2, Dataset 3, respectively), as shown at 208. Over three datasets, it is clear that Augmentation 2 helps prevent overfitting, however, it does not help with generalization compared to models without augmentation.

Interestingly, the overall validation accuracy without augmentation was significantly higher than the overall validation accuracy with Augmentation 2, with p<0.05 over the three datasets, as shown at 208. This finding contradicts results usually reported in computer vision where the overall validation accuracy without augmentation is lower than the overall validation accuracy with any augmentation methods.

Figure 3:
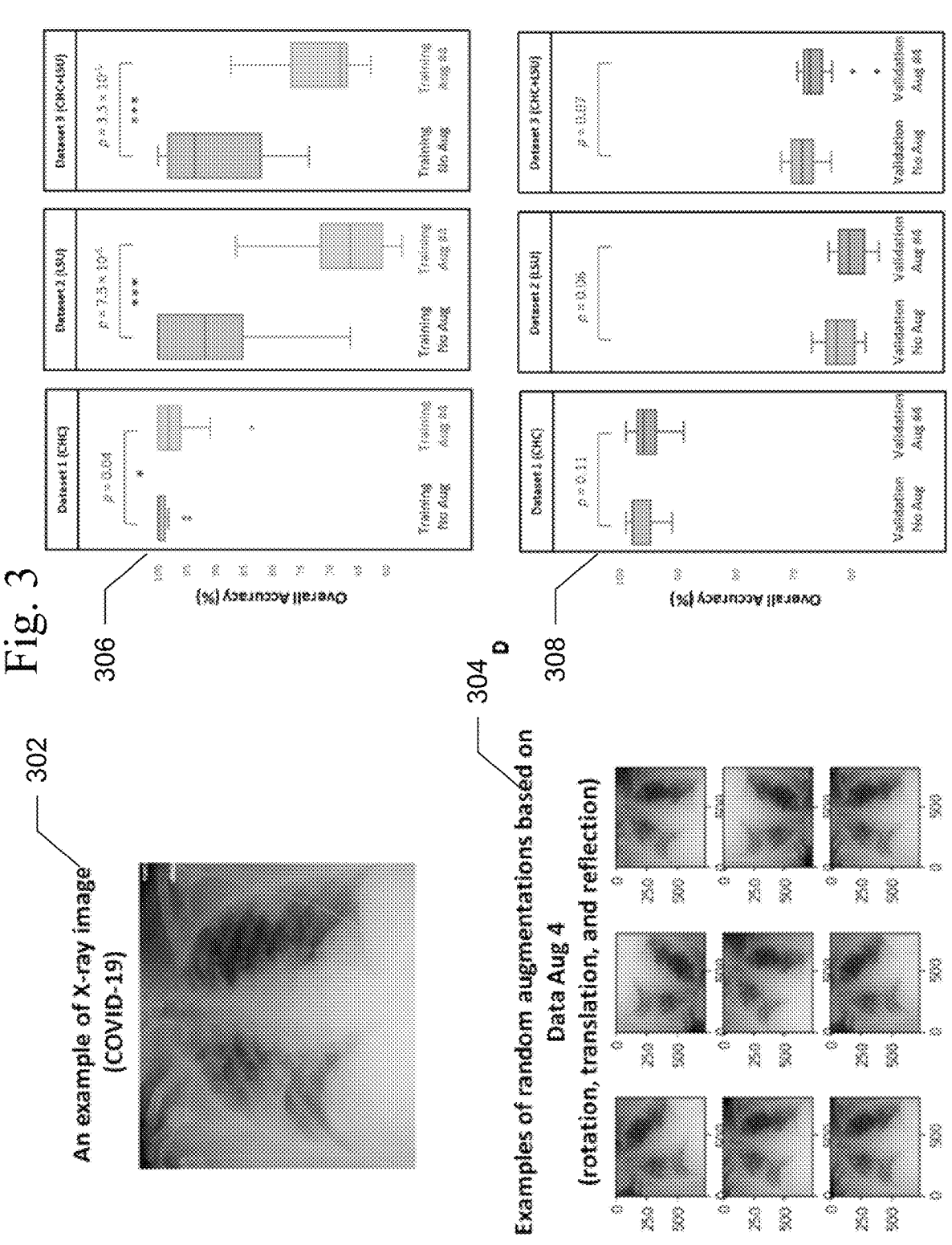
FIG. 3 shows the efficacy of an exemplary Data Augmentation on X-ray images with and without COVID-19, according to embodiments of the present techniques.

FIG. 3 shows the efficacy of Data Augmentation 4 on X-ray images 302 with and without COVID-19. An example of applying Data Augmentation 4, which includes rotation by 10 degree, translation, and horizontally reflection to a COVID-19 X-ray image 302. An exemplary comparison 304 of the overall accuracy of 17 deep neural networks to examine the efficacy of Data Augmentation 2 when applied to three datasets is shown. Exemplary boxplots 306 show the overall statistical different between training with and without augmentation over three datasets. Exemplary boxplots 308 show the overall statistical different between validation with and without augmentation. Note that results shown at 306, 308 are obtained from cross validation with K=10.

FIG. 3 shows the efficacy of Data Augmentation 4 on three datasets. Similar to Data Augmentation 2, the augmentation methods help prevent overfitting; however, it fails in generalization as its validation accuracy is less than without augmentation. It is worth mentioning that the overall validation accuracy without augmentation was not significantly different from the overall validation accuracy with Augmentation 4, as p=0.11, p=0.06, p=0.07, for Dataset 1, Dataset 2, Dataset 3, respectively. The performance of Augmentation 4 was ranked first compared to the other augmentation methods based on the MCC, as its average MCC=0.49 is closest to the MCC without augmentation MCC=0.51, as shown in Table 1.

Figure 4:
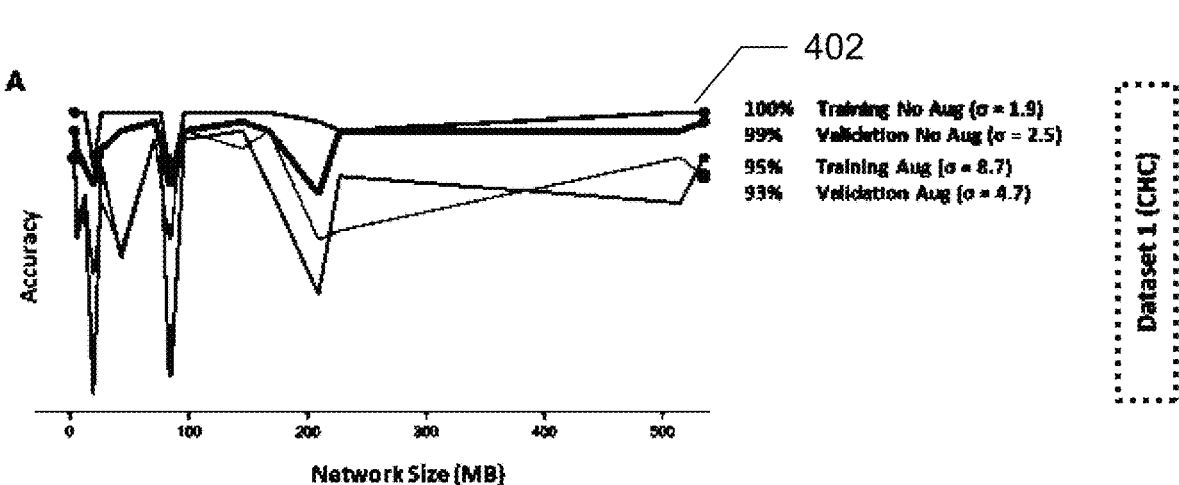
FIG. 4 shows the impact of an exemplary Data Augmentation on network architectures with smaller size, according to embodiments of the present techniques.
Figure 4:
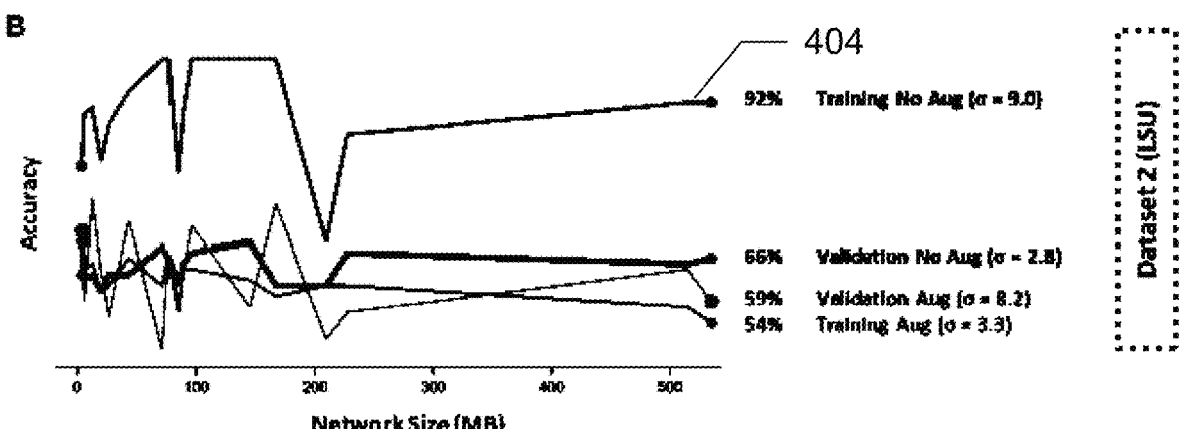
Figure 4:
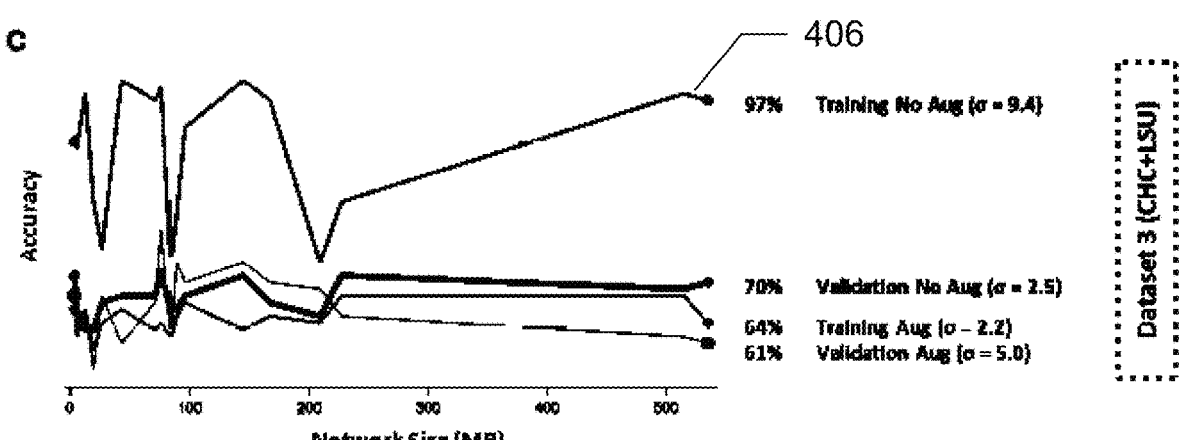

FIG. 4 shows the impact of Data Augmentation 2 on network architectures with smaller size, which led to unstable (fluctuating with high variance) performance. As the model size increases from 200 to 500 MB, the generalization accuracy becomes more stable. Small networks, <200 MB, have a limited capacity, which introduces an additional bias that could destabilize generalization, leading to overfitting. Interestingly, over all three datasets, the overall validation accuracy without augmentation is higher than the overall validation accuracy with Data Augmentation 2. In fact, the overall validation accuracy without augmentation was almost stable ($\sigma$=2.5, $\sigma$=2.8, $\sigma$=2.5, for Dataset 1 402, Dataset 2 404, and Dataset 3 406, respectively) and consistent over different network sizes compared to that with augmentation, where $\sigma$=4.7, $\sigma$=8.2, $\sigma$=5.0, for Dataset 1 402, Dataset 2 404, and Dataset 3 406, respectively, as shown in FIG. 4.

Figure 5:
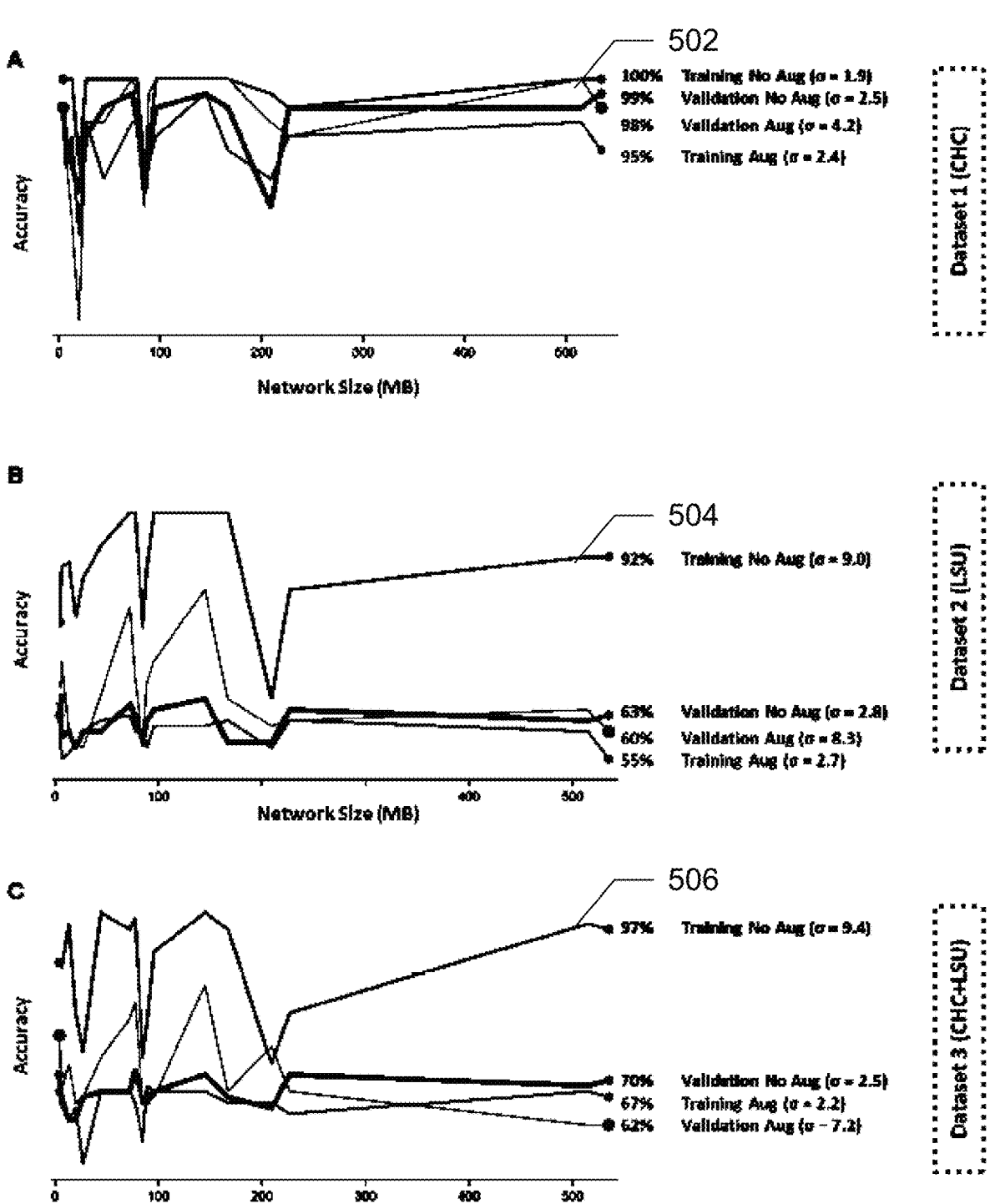
FIG. 5 shows stability of an exemplary Data Augmentation regardless of the network size over the CHC dataset, according to embodiments of the present techniques.

FIG. 5, at 502, shows that Data Augmentation 4 was relatively stable $\sigma$=2.5) regardless of the network size over the CHC dataset. Over the CHC, LSU, and CHC+LSU, the larger the network size, the accuracy of models with Data Augmentation 4 could get higher than without augmentation, as shown at 502, 504, 506. However, it is not a stable result, as $\sigma$=4.2 and $\sigma$=8.3 with augmentation compared to $\sigma$=4.2 and $\sigma$=8.3 without the augmentation step on Dataset 1 and Dataset 2, respectively. In other words, one large network size can improve the overall validation accuracy with augmentation 4. However, it does not mean that Data Augmentation 4 will have the same (or similar) effect using a different network. Stability over different sizes is vital to evaluate the impact of the data augmentation method.

A recently published model used an augmentation step that rotated the X-ray images by random angles in the range [−3, 3] degrees and resized the X-ray images by random scale factors in the range [1, 2]. We sought to remove the augmentation step of this algorithm and examine if our finding was valid. We then removed the augmentation step and reran the whole analysis to compare the impact of the data augmentation step.

As shown in FIG. 6, Method II resulted in 346 predictions that were correct when compared to cases that Method I did not predict. On the contrary, Method I resulted in 81 correct predictions that Method II did not predict. Thus, based on this 346:81 ratio, we may conclude that Method II performs substantially better than Method I. However, to quantify the impact, the accuracy and the statistical significance need to be reported. The accuracy of each method can be calculated as follow: Method I (Aug) accuracy=5, 469/5, 854=93.42% and Method II (No Aug) accuracy=5, 734/5, 854=97.95%. Based on accuracy calculation, Method II outperformed Method I, suggesting that adding the augmentation step is decreasing the detection accuracy. We then applied the McNemar's Test, and we obtained a 2 McNemar's statistic=163.2, with a p-value of 2.23×10-37, which is below the set significance threshold (=0.05) and lead to the rejection of the null hypothesis; we can conclude that the methods' performances are different. In fact, Method II significantly outperformed Method I. Researchers often blindly assume that applying any data augmentation step improves accuracy, but this is not always the case, and could be dependent on the application and augmented data utilized.

Clinical Perspective. Data augmentation is a great tool that can provide new images that preserve original features, but it can also generate noise that can be harmful to the training phase. As an example, applying rotations and flips for detecting a dog in an image, such as in ImageNet challenges, is considered "acceptable." On the contrary, applying the same geometrical augmentations for classifying a digit such as 6 vs. 9, is "not recommended". If the purpose was to recognize a dog in an image, then rotation with a wide range could be acceptable, but if the purpose was to detect COVID-19 in an X-ray image, then rotation could harm the training phase. Furthermore, the accuracy of the deep learning is heavily impacted by the rotation degree.

In computer vision, it seems that applying geometric augmentation steps such as rotation and reflection are generally "acceptable." However, applying the augmentation step must be sensible and plays an effective role in detecting the required pattern. In other words, the network trained with augmentation needs to be more robust and accurate than expected variations of the same X-Ray images. The augmentation step is a domain dependent, not an arbitrary step, that can be applied to all research fields in the same way.

Applying an augmentation without a clinical consideration may lead to achieving lower accuracy on the validation dataset. Below, we try to discuss different geometric augmentations and label them clinically "acceptable," "possible," "not recommended." This may help organize what to consider and what not to consider during the development of a deep learning algorithm in terms of data augmentation.

After augmentation, the generated augmented images do not get labeled by radiologists to confirm that their validity. Getting radiologists to label original X-ray images is challenging already given their limited time. The requirement to label the augmented images is not practical and perhaps cannot be facilitated.

To close this gap, and speed up the process, between the computer scientists and clinicians, we sought the opinion of radiologists on the different geometric augmentation steps. This could help in designing new algorithmic approaches for detecting COVID-19 using X-ray images in the near future. Presented here is some of that clinical input for consideration:

1. Reflection: Reflection in x-axis is a step that is unusual, as the x-ray is flipped upside down. This step is "not recommended," as it is an adding unnecessary noise that may mislead the learning algorithm. For example, applying this step for digit recognition is "not recommended," the neural network will not be able differentiate between number 6 and number 9. Reflection in y-axis does not change Posterior-Anterior (PA) to Anteroposterior (AP). However, it would lead to non-physiologic images (e.g., heart in the right thorax rather than the left thorax), which might confound learning and is "not recommended." There is no existing data augmentation technique that can simulate the differences between PA and AP chest x-ray images, since relative positioning in patient, x-ray tube, and detector produce differential magnification and affect edge definition.

2. Rotation: Applying rotation to X-ray images could be helpful. However, it depends on the range of rotation a severe rotations can be harmful. Slight rotations such as between −5 and 5 are seen in clinical practice, however, severe rotations such as between −90 and 90 are "not recommended," as the generated X-rays are unlikely to be encountered, and can add unnecessary noise to the learning model.

3. Scaling: Scaling can be in x-axis, y-axis, or both. When large scaling (>×1) is applied, regardless of the direction, the augmented X-ray image will be a stretched version of the original X-ray. When a small scaling (<×1) is applied, the size augmented X-ray will be less than the original image. An equal scaling in x-axis and γ-axis is "possible," however, scaling in only the x-axis or y-axis can be considered "not recommended" clinically.

4. Shearing: Shearing can be applied to x-axis, y-axis, or both directions. It is measured as an angle in degrees, and is in the range −90 to 90. The augmented X-ray images look like the original skewed in the specified direction(s). This step can be considered "not recommended," as it produces images that do not exist clinically.

5. Translation: Translation or "Shifting" X-ray images up, down, left, or right, could be a useful augmentation step. This is because the X-ray images do not always produce lungs in the center of the image. This can depend on the patient's position, as well as the radiographic unit itself, such as if it is portable. Having X-ray images where the lungs are centered could lead to a more robust COVID-19 detector. As such, this step seems to be "acceptable" clinically as it is observed. However, there is no clearly recommended range for translation.

Scaling augmentation may be a useful method in computer vision applications, especially for capturing a certain pattern in an image. However, for the purpose of detecting COVID-19, it can negatively impact detection accuracy. Unfortunately, applying rotation and scaling augmentations to deep neural networks can reduce the classification accuracy. So far, we have tested a subset of data augmentation methods, specifically geometric transformations. There are other augmentation methods that need to be tested, such as color space augmentations, feature space augmentations, and adversarial training.

Figure 8:
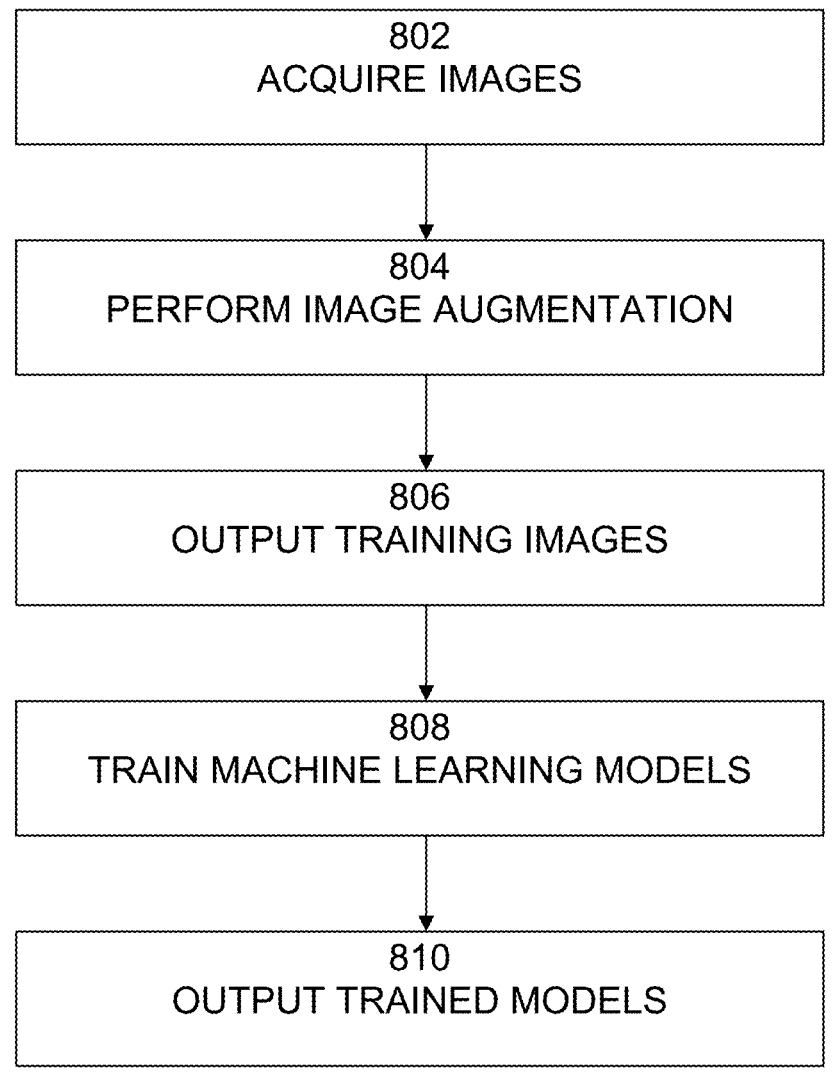
FIG. 8 is an example of a method according to embodiments of the present techniques.

An example of a method 800 according to embodiments of the present techniques is shown in FIG. 8. Method 800 begins with 802, in which images may be acquired from imaging systems, such as X-ray images, CT images, MRI images, etc., as well as from databases of labeled or unlabeled images. At 804, image augmentations, such as those described above, may be performed to the acquired images so as to generate additional images that may be used for training. At 806, training images are output, which may include a plurality of images, including acquired images and images generated by image augmentation. At 808, the training images may be used to train machine learning models so as to recognize medical conditions from newly obtained images. At 810, the trained machine learning models may be output.

Figure 7:
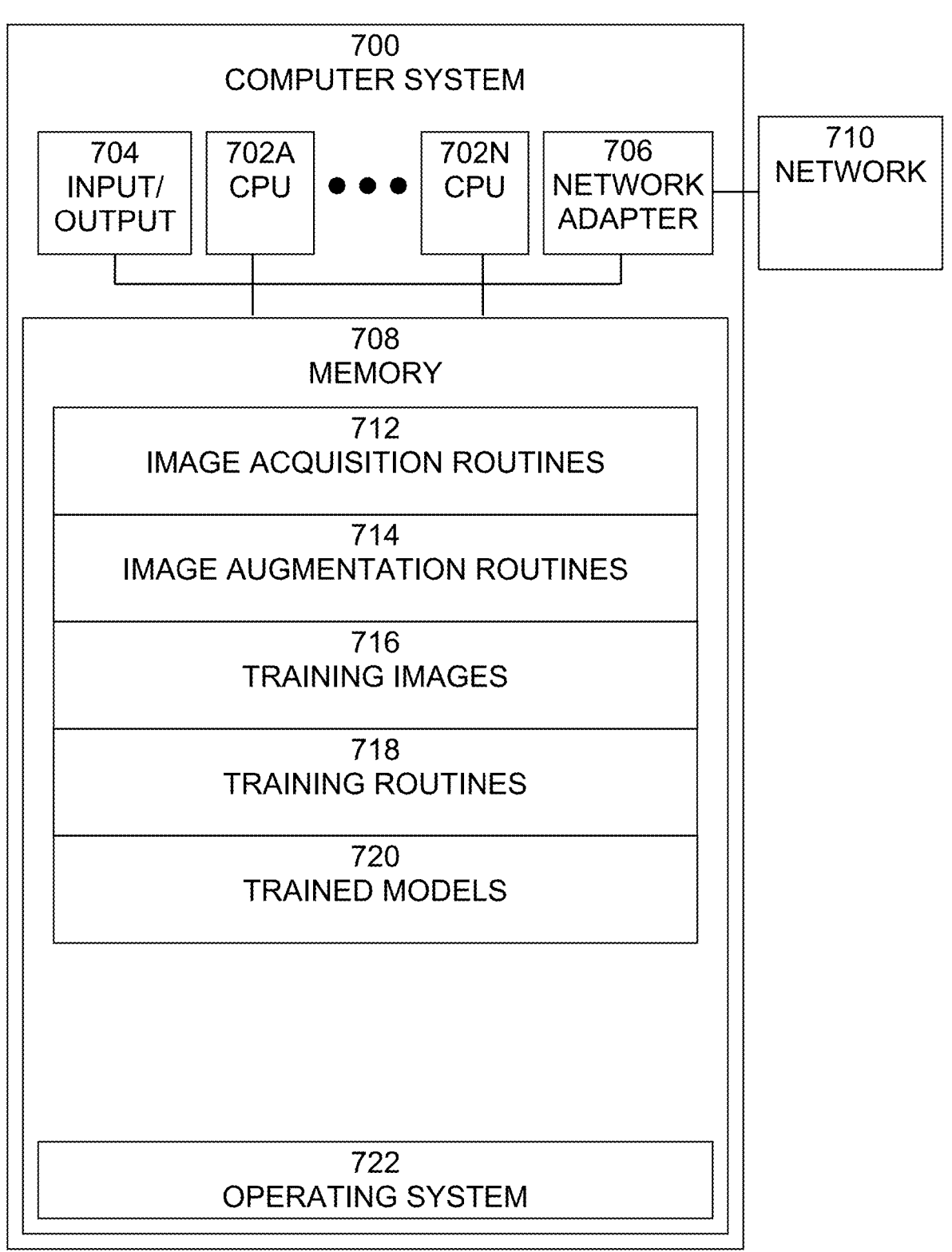
FIG. 7 is an exemplary block diagram of a computer system, in which processes involved in the embodiments described herein may be implemented.

An exemplary block diagram of a computer system 700, in which processes involved in the embodiments described herein may be implemented, is shown in FIG. 7. Computer system 702 may be implemented using one or more programmed general-purpose computer systems, such as embedded processors, systems on a chip, personal computers, workstations, server systems, and minicomputers or mainframe computers, or in distributed, networked computing environments. Computer system 702 may include one or more processors (CPUs) 702A-702N, input/output circuitry 704, network adapter 706, and memory 708. CPUs 702A-702N execute program instructions in order to carry out the functions of the present communications systems and methods. Typically, CPUs 702A-702N are one or more microprocessors, such as an INTEL CORE® processor. FIG. 7 illustrates an embodiment in which computer system 702 is implemented as a single multi-processor computer system, in which multiple processors 702A-702N share system resources, such as memory 708, input/output circuitry 704, and network adapter 706. However, the present communications systems and methods also include embodiments in which computer system 702 is implemented as a plurality of networked computer systems, which may be single-processor computer systems, multi-processor computer systems, or a mix thereof.

Input/output circuitry 704 provides the capability to input data to, or output data from, computer system 702. For example, input/output circuitry may include input devices, such as keyboards, mice, touchpads, trackballs, scanners, analog to digital converters, etc., output devices, such as video adapters, monitors, printers, etc., and input/output devices, such as, modems, etc. Network adapter 706 interfaces device 700 with a network 710. Network 710 may be any public or proprietary LAN or WAN, including, but not limited to the Internet.

Memory 708 stores program instructions that are executed by, and data that are used and processed by, CPU 702 to perform the functions of computer system 702. Memory 708 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 708 may vary depending upon the function that computer system 702 is programmed to perform. In the example shown in FIG. 7, exemplary memory contents are shown representing routines and data for embodiments of the processes described above. However, one of skill in the art would recognize that these routines, along with the memory contents related to those routines, may not be included on one system or device, but rather may be distributed among a plurality of systems or devices, based on well-known engineering considerations. The present systems and methods may include any and all such arrangements.

In the example shown in FIG. 7, memory 708 may include memory contents for self-aware mobile systems and autonomous sensor platforms. Memory contents may include data image acquisition routines 712, image augmentation routines 714, image interpretation routines 716, output routines 718, and operating system 720. Image acquisition routines 712 may include software to acquire images from imaging systems, such as X-rays, CT scans, MRI scans, etc., as well as software to acquire images from databases of labeled or unlabeled images. Image augmentation routines 714 may include software to perform image augmentation, such as those described above, to images acquired by image acquisition routines 712, so as to generate additional images that may be used for training. Training images 716 may include a plurality of images, including images acquired by image acquisition routines 712 and images generated by image augmentation routines 714. Training routines may 718 may include software to use training images 716 to train machine learning models so as to recognize medical conditions from newly obtained images. Operating system 722 may provide overall system functionality.

As shown in FIG. 7, the present communications systems and methods may include implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multitasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A system for detecting medical conditions comprising:
an image acquisition component adapted to acquire a plurality of images of persons, at least some of whom have a medical condition;
an image augmentation component adapted to when the medical condition is not a virological disorder generate a plurality of additional images from the acquired plurality of images using a plurality of image augmentation methods and when the medical condition is a virological disorder, not generate the plurality of additional images so as to improve accuracy of a machine learning model in recognizing presence of a virological disorder in images; and
a training component adapted to train the machine learning model, when the medical condition is not a virological disorder using the acquired plurality of images and the generated plurality of additional images to form a trained machine learning model, and when the medical condition is a virological disorder using the acquired plurality of images to form the trained machine learning model.

2. The system of claim 1, wherein the plurality of image augmentation methods comprises at least some of: translation in x-axis, translation in y-axis, random shear in x-axis, random shear in y-axis, random rotation, horizontal reflection, vertical reflection, scaling in x-axis, scaling in y-axis, and any combination thereof.

3. The system of claim 2, wherein the acquired plurality of images comprises at least one of X-ray images, CT images, and MRI images.

4. The system of claim 1, wherein the virological disorder is COVID-19.

5. A method for detecting medical conditions, implemented in a computer system comprising a processor, memory accessible by the processor, and program instructions and data stored in the memory to implement the method comprising:
acquiring a plurality of images of persons, at least some of whom have a medical condition;
when the medical condition is not a virological disorder:
generating a plurality of additional images from the acquired plurality of images using a plurality of image augmentation methods, and
training a machine learning model using the acquired plurality of images and the generated plurality of additional images to form a trained machine learning model; and
when the medical condition is a virological disorder:
not generating the plurality of additional images so as to improve accuracy of the machine learning model in recognizing presence of a virological disorder in images.

6. The method of claim 5, wherein the plurality of image augmentation methods comprises at least some of: translation in x-axis, translation in y-axis, random shear in x-axis, random shear in y-axis, random rotation, horizontal reflection, vertical reflection, scaling in x-axis, scaling in y-axis, and any combination thereof.

7. The method of claim 6, wherein the acquired plurality of images comprises at least one of X-ray images, CT images, and MRI images.

8. The method of claim 5, wherein the virological disorder is COVID-19.

9. A non-transitory computer program product for detecting medical conditions, the computer program product comprising a non-transitory computer readable storage having program instructions embodied therewith, the program instructions executable by a computer, to cause the computer to perform a method comprising:
acquiring a plurality of images of persons, at least some of whom have a medical condition;
when the medical condition is not a virological disorder:
generating a plurality of additional images from the acquired plurality of images using a plurality of image augmentation methods, and
training a machine learning model using the acquired plurality of images and the generated plurality of additional images to form a trained machine learning model; and
wherein when the medical condition is a virological disorder:
not generating the plurality of additional images so as to improve accuracy of the machine learning model in recognizing presence of a virological disorder in images.

10. The computer program product of claim 9, wherein the plurality of image augmentation methods comprises at least some of: translation in x-axis, translation in y-axis, random shear in x-axis, random shear in y-axis, random rotation, horizontal reflection, vertical reflection, scaling in x-axis, scaling in y-axis, and any combination thereof.

11. The computer program product of claim 10, wherein the acquired plurality of images comprises at least one of X-ray images, CT images, and MRI images.

12. The computer program product of claim 9, wherein the virological disorder is COVID-19.

* * * * *